(12) United States Patent
Rutten et al.

(10) Patent No.: US 6,823,217 B2
(45) Date of Patent: Nov. 23, 2004

(54) METHOD AND APPARATUS FOR IMPARTING CURVES IN ELONGATED IMPLANTABLE MEDICAL INSTRUMENTS

(75) Inventors: Jean J. G. Rutten, Bocholtz (NL); Karel F. A. A. Smits, Munstergeleen (NL)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/934,189

(22) Filed: Aug. 21, 2001

(65) Prior Publication Data

US 2003/0040666 A1 Feb. 27, 2003

(51) Int. Cl.$^7$ .................................................. A61N 1/00
(52) U.S. Cl. ........................ 607/122; 607/116; 607/119
(58) Field of Search ................................ 607/116, 119, 607/122; 600/372, 374; 606/41, 49, 50

(56) References Cited

U.S. PATENT DOCUMENTS

| | | | |
|---|---|---|---|
| 3,452,740 A | 7/1969 | Muller | 128/2 |
| 4,136,703 A | 1/1979 | Wittkampf | 128/419 P |
| 4,381,013 A | 4/1983 | Dutcher | 128/785 |
| 4,458,677 A | 7/1984 | McCorkle, Jr. | 128/786 |
| 4,479,500 A | 10/1984 | Smits | 128/786 |
| 4,488,561 A | 12/1984 | Doring | 128/786 |
| 4,506,680 A | 3/1985 | Stokes | 128/786 |
| 4,577,642 A | 3/1986 | Stokes | 128/784 |
| 4,606,118 A | 8/1986 | Cannon et al. | 29/825 |
| 4,606,350 A | 8/1986 | Frost | 128/419 PG |
| 4,676,249 A | 6/1987 | Arenas et al. | 128/657 |
| 4,677,990 A | 7/1987 | Neubauer | 128/786 |
| 4,711,281 A | 12/1987 | Kessel et al. | 144/256.1 |
| 4,815,478 A | 3/1989 | Buchbinder et al. | 128/772 |
| 4,898,577 A | 2/1990 | Badger et al. | 604/53 |
| 4,940,062 A | 7/1990 | Hampton et al. | 128/772 |
| 5,040,543 A | 8/1991 | Badera et al. | 128/772 |
| 5,170,787 A | 12/1992 | Lindegren | 128/642 |
| 5,231,996 A | 8/1993 | Bardy et al. | 128/785 |
| 5,327,906 A | 7/1994 | Fideler | 128/772 |
| 5,439,006 A | 8/1995 | Brennen et al. | 128/772 |
| 5,545,200 A | 8/1996 | West et al. | 607/122 |
| 5,562,619 A | 10/1996 | Mirarchi et al. | 604/95 |
| 5,662,119 A | 9/1997 | Brennen et al. | 128/772 |
| 5,728,148 A | 3/1998 | Bostrom et al. | 607/116 |
| 5,824,031 A | 10/1998 | Cookston et al. | 607/122 |
| 6,059,739 A | 5/2000 | Baumann | 600/585 |
| 6,223,087 B1 | 4/2001 | Williams | 607/119 |

*Primary Examiner*—Rosiland Rollins
(74) *Attorney, Agent, or Firm*—Michael C. Soldner; Girma Wolde-Michael

(57) ABSTRACT

A medical instrument including a body extending between proximal and distal ends and enclosing an elongated, inelastic, pull wire extending between a pull wire proximal end affixed at a point at or near the proximal end and a pull wire distal end affixed at or near the distal end. The wire extends through a lumen off-set from the instrument axis and through a distal segment of the body that is to be curved for deflection at the distal end. A proximal segment of the instrument axially stretches when tension is applied to increase the length of the proximal segment from a relaxed length. A hand-held tool engages the proximal and distal ends of the proximal segment and manually applies a selective amount of tension that stretches the proximal segment from its relaxed length.

45 Claims, 6 Drawing Sheets

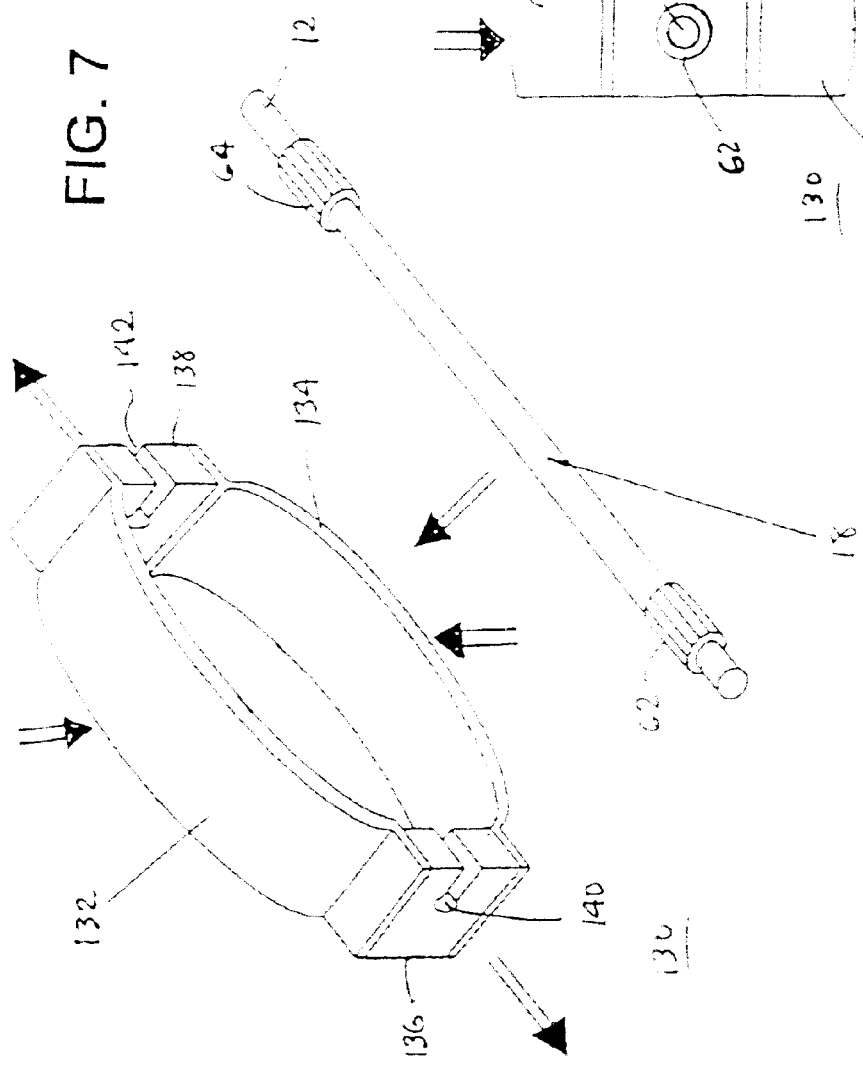
FIG. 7
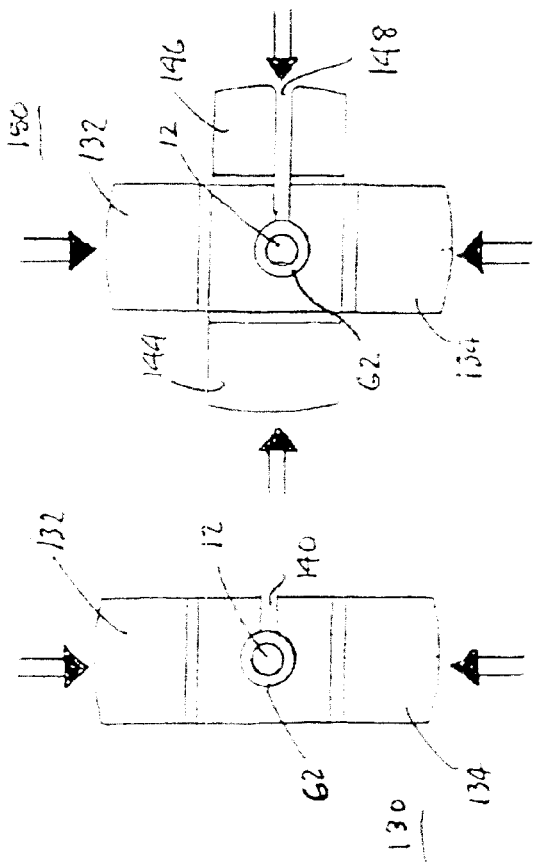
FIG. 8
FIG. 9

METHOD AND APPARATUS FOR IMPARTING CURVES IN ELONGATED IMPLANTABLE MEDICAL INSTRUMENTS

FIELD OF THE INVENTION

The present invention pertains to elongated medical instruments adapted to be permanently or temporarily implanted in the mammalian body or used to access a site in the body to facilitate introduction of a further medical device, and particularly to methods and apparatus for deflecting the distal end and imparting curves in distal segments of such medical instruments within the body by manipulation of a proximal segment of the instrument outside the body.

BACKGROUND OF THE INVENTION

A wide variety of elongated medical instruments that are adapted to be permanently or temporarily implanted in the mammalian body, usually the body of a human patient, or used to access a site in the body to facilitate introduction of a further medical device. Such elongated medical instruments have an instrument body extending between instrument body proximal and distal ends, and a distal segment of the instrument body is advanced to a remote site in the body by manipulation of a proximal segment of the instrument body or a handle or stylet or the like extending from the instrument body proximal end located outside the body.

Elongated medical instruments include implantable medical electrical leads, catheters, guide wires, and the like. In the case of a medical electrical lead, the lead body proximal end is coupled to an implantable pulse generator (IPG) or monitor that is then implanted subcutaneously or to an external medical device located outside the body and electrical signals are conducted to or from the remote site in the body through one or more lead conductor. Catheters typically extend through the patient's skin and are coupled with external diagnostic or therapeutic equipment or are used to introduce other elongated medical instruments or fluids or the like, or to withdraw fluids or measure pressure, or the like, through a catheter lumen open at the accessed remote site. Certain catheters, e.g., electrophysiology ablation and mapping catheters, also deliver electrical energy or conduct electrical signals of the body. Other catheters include pulmonary artery catheters, central venous catheters, diagnostic coronary catheters, intra-aortic balloon pump catheters, balloon tipped (PTCA)/angioplasty catheters, and cardiac stent delivery catheters. The terms "catheter" and "lead" are often interchanged in these and other contexts. Guide wires are small diameter wires that are directed through tortuous pathways to provide for advancement of medical leads or catheters over-the-wire. Certain guide wires are also designed to function as a micro-catheter for infusion of fluids through a guide wire lumen. Other guide wires include insulated electrical conductors connected at the guide wire proximal end with an external medical device to deliver electrical energy for tissue stimulation or to conduct electrical signals of the body to the external medical device. Hence, in the following discussion, the terms electrical medical leads, catheters and guide wires comprise and can be used interchangeably with elongated medical instruments.

In many cases, the introduction of such elongated medical instruments to a remote site in the body is effected through a skin incision accessing an incision into a blood vessel, whereby the instrument body is advanced through a vascular pathway until the distal segment or the instrument body distal end are located at the remote site. Such advancement is often through a tortuous pathway having twists and turns requiring the capability to impart a curve or deflect the instrument body distal end to facilitate advancement. Therefore, the introduction of such elongated medical instruments through vascular pathways or other tortuous pathways in the body is facilitated by a wide variety of techniques and mechanisms that have been developed to impart curves in the distal segment of the instrument body or to deflect the instrument body distal end.

Currently, during the implantation of a permanent cardiac pacemaker or an implantable cardioverter/defibrillator (ICD), endocardial cardiac leads, e.g., pacing leads and/or cardioversion/defibrillation leads, are introduced into a vein either via a cut down or percutaneous sheath introduction. The cardiac leads are advanced under fluoroscopy into either the right atrium, right ventricle (or both in the case of a dual chamber pacemaker or ICD implantation) or into a cardiac vessel, e.g., the coronary sinus and great vein. Generally speaking, it is highly desirable that such cardiac leads be so flexible through their length that they are capable of flexing with the movement of the heart and other muscular movement so as to void the fracture of the lead body due to its cumulative stressing. Such cardiac lead bodies are generally too limp to be advanced axially on their own through the vascular pathway to the desired site in a heart chamber or vessel. It has been commonplace for many years to employ thin wire stiffening stylets extended down a lumen of the lead body to stiffen the entire assembly so that it can be pushed axially through the venous pathway. Then, the distal pace/sense electrodes or cardioversion/defibrillation electrodes (herein "cardiac electrodes") must be fixed at the preferred site in the heart chamber or vessel to operate most efficaciously and to prevent dislodgement. The introduction and fixation of these cardiac leads is the most time consuming and difficult aspect of the implantation.

At the outset, a straight or slightly curved stiffening stylet is first extended into the lead body lumen within the cardiac lead in order to give the cardiac lead sufficient column strength and rigidity to be pushed through the tributary veins and typically into the subclavian vein. The stylet may be left straight or provided with a certain degree of curvature to facilitate the introduction through these veins and through the initial curvatures thereof. Thereafter, and from time to time, as the physician directs the distal tip of the cardiac lead in a tortuous path leading to the right heart through the superior vena cava (SVC), it may be necessary to withdraw the stylet and either substitute a new stylet or impart a different curvature to the distal portion of the stylet, reinsert the stylet, and advance the distal portion of the lead a bit further until another obstacle to advancement is encountered.

When the distal cardiac electrodes are to be placed in the right ventricle, the physician manually fashions a curve at the tip of another stylet that is inserted into the lead body lumen to advance the assembly through the tricuspid valve into the right ventricle. Most physicians continue advancing the lead with the curved tip stylet in place into the pulmonary artery outflow track to confirm right ventricle access and to rule out the possibility of entrance into the coronary sinus or coronary vein, which can mimic the appearance of a right ventricle placement under fluoroscopy. The conventional practice requires the physician to then remove the curved stylet and partially re-advance the original or another straight stylet into the lead body lumen, once the physician has confirmed that the lead is in fact in the pulmonary outflow track. The cardiac lead is then carefully pulled back under direct fluoroscopic observation until the lead body distal segment drops from the proximal portion of the pulmonary artery to the floor of the right ventricle. The physician then advances the stylet to its fully advanced position within the lead body lumen and advances the lead distal end into the right ventricular apex. Passive or active fixation mechanisms at the lead body distal end then effect fixation with the trabeculae or the myocardium to acutely maintain the cardiac electrode electrode(s) at the operative site.

In the case of atrial lead placement, the lead body distal end is typically lodged or affixed in the right atrial appendage which results in the lead body extending into the right atrium via the SVC and then bent through about a 180° or greater bend.

Over the years, many atrial cardiac lead designs and atrial cardiac lead introduction tools and techniques have been proposed or clinically used to both achieve this orientation and to fix the cardiac lead body distal end within the atrial appendage and avoid dislodgement. Initially, such atrial cardiac leads were formed with a permanent "J"-shaped bend to facilitate both the positioning and the retention of the atrial electrode in the patient's atrial appendage as taught, for example, in U.S. Pat. No. 4,136,703. Insertion of these "J"-shaped leads is greatly facilitated through the use of a straight solid inner stylet which, in this case, straightens the bend normally fixed within the distal end of the lead itself to the extent that the stylet is advanced into or retracted from the lead body lumen.

Moreover, it has been proposed to combine atrial and ventricular leads together or in a cooperative relation to provide a "single pass" implantation of both leads as set forth in U.S. Pat. Nos. 4,458,677 and 4,479,500 and patents referenced therein. Such proposed single pass AV leads have not gained acceptance due to their complicated construction, use and size.

J-shaped atrial leads have largely been abandoned in favor of reduced diameter lead bodies that cannot accommodate shape-forming structures and the use of the straightening stylet as described above. Today, the small diameter cardiac lead body is normally straight, and the lead body distal end is typically aimed into the atrial appendage employing multiple insertions of relatively straight and curved stylets. The electrode bearing lead body distal end is fixed in the atrial appendage by means of an active fixation screw or passive fixation tines. However, dislodgements can occur before the fixation is effected when a stylet is withdrawn proximally as the stylet may bind against the lead body lumen in the region of the bend.

Thus, there are multiple exchanges of straight stylets and curved stylets which have been bent according to the physician's choice in a typical cardiac lead implantation in the right atrium and ventricle. Similar techniques and multiple stylets are avoided to advance a cardiac lead distal segment into the coronary sinus and great vein. Stylets are typically formed of solid wire, typically about 0.014–0.018 inches in diameter. During handing, such stylets can easily become bent or kinked, and thereafter cause great difficulty when an attempt is made to reinsert them through the narrow inner diameter of the lead body lumen, which may only be 0.019 inch in the case of a stylet of 0.018 inch diameter, thereby providing no more than 0.0005 inch clearance around the circumference. The continual withdrawal and reintroduction of stylets is time consuming and offers the potential of damaging the lead in the process.

Moreover, it is undesirable to contaminate the lead body lumen with blood during this process because drying blood can form a strong adhesive bond between the stylet and the lumen wall, making stylet removal impossible and rendering the lead unusable. Because the surgeon is working through an open wound, even the most fastidious surgeon will have blood on his gloves that can be transferred to the stylet. The blood congeals, and because of the small clearance, even a few drops of blood are sufficient to causing jamming of the stylet inside the lead body lumen. When the stylet jams in the lead body lumen, kinking of the stylet within the lead can occur, which kinks, in turn, will create new jams or problems with the insertion and retraction of the stylet from the lead body lumen. In some cases, the jamming is so severe that the cardiac lead must be removed from the heart for fear of insulation puncture, discarded, and a new lead implanted, thereby at least doubling the lead cost used in the procedure as well as operative time. The overall result of such difficulties is that operative time is greatly increased which results in increased time delay, associated cost, and prolonged X-ray exposure to the patient under continuous fluoroscopy as well as prolonged scattered X-ray exposure to the operating room staff due to procedural time delays. These problems with the use of multiple stiffening stylets have been recognized in the art as set forth in U.S. Pat. Nos. 4,136,703, 4,381,013, 4,677,990,5,662,169, 5,824,031, and 6,059,739, for example.

Many proposals have been advanced to reduce the number of stylets and the consequent number of times that stylet removal and re-insertion that are needed in the procedure. One approach has been to employ deflectable stylets wherein the stylet distal segment can be deflected or curved while within the lead body lumen from the proximal end thereof. Two-piece stylets that comprise a straight, tubular outer member and a curved inner member received within the outer member lumen enabling relative movement of the inner and outer members are disclosed in the above-referenced '703 and '013 patents for straightening a J-shaped bend and in U.S. Pat. No. 5,728,148. The outer tubular member of the '013 patent enables the transmission of torque applied by the implanting physician at the proximal end to be transmitted to a fixation helix located at the lead body distal end lead to screwed the helix into endocardial tissue. Alternatively, two-piece stylets comprising a curved outer member and a relatively straight inner member are also known to the art, as disclosed in U.S. Pat. Nos. 4,676,249 and 5,040,543. In such composite stylets, the relative position of the inner member with respect to the outer member determines the degree to which the curved member (inner or outer) is allowed to display its preset curvature.

A commonly employed approach to providing controllable deflection of the distal end segments of catheters and guide wires employs a generally straight outer sheath and a pull or push or push-pull wire extending through a lumen of the outer sheath to an attachment point at the sheath distal end. The wire is pushed or pulled on at its proximal end typically through a handle that is permanently or removably attached to the catheter or guide wire proximal end. The proximal retraction or distal advancement of the pull or push wire, respectively, causes at least a distal segment of the outer sheath to bend or deflect. Examples of such deflection mechanisms in catheters can be found in U.S. Pat. Nos. 4,815,478, 4,898,577, 4,940,062, and 5,545,200. U.S. Pat. Nos. 4,815,478 and 4,940,062 disclose the use of push-pull wires extending through guide wire lumens for deflecting the guide wire distal end by manipulating a handle at the guide wire proximal end. Deflectable stylets intended to be inserted into cardiac lead body lumens employing this type of deflection mechanism are disclosed in U.S. Pat. Nos. 5,662,119, 5,170,787, and 5,327,906, 5,439,006, and 6,059,739.

The above-referenced '990 patent discloses the combination of a removable stylet and at least one non-conductive thread that function like a pull wire having very low elasticity coupled near the cardiac lead body distal end or at selective locations along the lead body. The thread extends from the lead body lumen proximal end opening through a proximal segment of the lead body lumen and then is passed through the turns of the lead conductor coil and extends distally through a distal segment alongside the conductor within the lead body sheath to the distal attachment point outside the conductor whereby the thread axis is offset from the coiled wire conductor axis. The cardiac lead is introduced into the right atrium with the straight stylet inserted in the lead body lumen alongside the thread. A curvature is induced in the lead body distal segment by applying traction to the thread proximal end exiting the lead body proximal end opening thereby pulling the thread taut and proximally. The curvature is dictated by the length of the distal segment where the thread extends in the space between the outer insulation sheath and the coiled wire conductor. The stylet is described as having portions of reduced thickness along a distal segment parallel with the distal segment of the lead body where the thread extends outside the lead body lumen to achieve easier bending. The '990 patent addresses concerns raised by the conventional technique of withdrawing, imparting a new curve, and reinserting the stiffening stylet during the implantation procedure. However, the stylet could bind in the lead body lumen with the thread upon retraction of the stylet and dislodge the lead body distal end segment. Also, the thread must be cut off before the lead body proximal end is attached to the IMD, rendering it inaccessible and presenting an obstacle to reinsertion of a stylet should that become necessary at some point later in the procedure or during the chronic implantation to correct a dislodgement or to remove the cardiac lead.

Moreover, the physician is required to employ both hands in order to manipulate the separate thread, the stylet extending proximally from the lead body lumen in the '990 patent and to hold the lead body proximal end steady. Similarly, the physician usually uses two hands to manipulate the deflectable stylets and the two-piece stylet of the '013 patent, for example, as well as the conventional one-piece stylets. It is usually necessary to manipulate the lead and stylet to advance and withdraw the stylet and rotate the lead body in the advancement of the lead body through the venous pathway and the lead body distal end into particular desired sites for lodging the electrodes.

Single-handed manipulation of such elongated medical instruments has been proposed but usually requires use of a bulky handle that enlarges the overall diameter of the instrument at the proximal end For example, U.S. Pat. No. 3,452,740 discloses a spring guide manipulator for imparting a curvature and rotation in a spring guide by one-handed use of a manipulative handle. The spring guide wire includes the conventional inner straight wire coupled to the distal end of the coiled wire of the distal portion of the spring wire guide. When the handle is attached to a guide wire and a catheter is fitted over the guide wire, it is reported that the handle may be employed to both rotate the guide wire and catheter as well as place a curve in the distal portion of the catheter. The above-referenced '662 and '739 patents as well as U.S. Pat. No. 5,170,787 disclose steerable stylets particularly for use in cardiac lead body lumens for selectively adjusting the curvature of the lead body that are manipulated by one hand operation, but are relatively complex and costly.

While all of the mechanisms disclosed in the above cited prior art patents are at least to some degree workable, there is still a perceived need for a mechanism that is simple, inexpensive to manufacture, does not excessively increase the elongated medical instrument body diameter, and can be manipulated using one hand to control the deflection and imparted curvature of the instrument body distal segment More significantly, there is a need for a such a mechanism that eliminates the need for separate curved stylets used to deflect and impart curves in the medical instrument distal segment and which provides a wide degree of dynamic curvature to the elongated medical instrument being advanced by the physician.

SUMMARY OF THE INVENTION

The invention is therefore directed to improvements in such elongated medical instruments that eliminate the need for separate stylets used to deflect and impart curves in the instrument distal segment and wherein the degree of deflection and curvature can be controlled using one hand.

In accordance with the present invention, the elongated medical instrument comprises an instrument body extending a predetermined length between instrument body proximal and distal ends and enclosing an elongated, inelastic, pull wire extending between a pull wire proximal end affixed at a point at or near the instrument proximal end and a pull wire distal end affixed at or near the instrument body distal end. The pull wire extends through a pull wire lumen that is off axis in a radial direction from the medical instrument axis and through a distal segment of the lead body that is to be curved so as to deflect the instrument distal end. The instrument body is formed of an elastic material at least in a proximal segment thereof that can be stretched or extended axially when tension is applied between proximal and distal ends of the proximal segment so as to increase the length of the proximal segment from its relaxed length. The applied tension is transferred to the inelastic pull wire which counters the extension of the proximal segment by bending the instrument body distal segment in the radial direction away from the instrument body axis. The proximal segment can either be "in-line" with the distal segment or can be formed as a side arm or branch of the proximal portion of the lead body that remains outside the body during implantation.

The elongated medical instrument further comprises a stylet lumen that extends from a stylet lumen proximal end opening at the instrument body proximal end to a stylet lumen distal end at the instrument distal end or in the instrument body distal segment. A stiff, straight stylet is introduced through the stylet lumen so that the degree and length of curvature induced in the distal segment depends upon the length of the stylet advanced through a proximal portion of the distal segment while tension is applied to the proximal segment. The stylet lumen is preferably offset radially from the lead body axis and 180° displaced from the pull wire lumen and pull wire.

Preferably, the proximal segment is adapted to be fitted into a hand-held tool that engages the proximal and distal ends of the proximal segment and applies a selective amount of tension that stretches the proximal segment from its relaxed length upon manual manipulation of the hand-held tool. Distance limiting stops that limit the maximal lengthening of the proximal segment and force limiting springs are preferably formed in certain of the hand-held tools Preferably, the distal segment of the instrument body is formed of a relatively inelastic material that resists axial stretching or contraction, and the proximal segment is formed of a more elastic material that is capable of elastically stretching axially over the maximal length of the proximal segment without any damage. The distal segment may compress axially slightly when the proximal segment is stretched axially.

One preferred embodiment of the elongated medical instrument comprises a cardiac lead particularly adapted to be placed in the right atrium or in the coronary sinus or the right ventricle for cardioversion/defibrillation and/or pacing in the right atrium or in the coronary sinus or in the right ventricle, respectively. In a unipolar embodiment, the lead conductor extending between a proximal connector pin and a distal cardiac electrode is preferably formed of a loose wound coiled wire fitted within the stylet lumen. The stiffening stylet extends through the coil lumen, and the coil turns are capable of stretching and compressing axially within the stylet lumen as the proximal segment is stretched and returns to its normal relaxed length.

In one bipolar or multi-polar embodiment, wherein one or more additional distal cardiac electrode and proximal connector element are coupled together by a respective lead conductor, the pull wire can be attached to and function as the lead conductor between a respective connector element and cardiac electrode.

In a further preferred embodiment, the present invention is implemented into a single pass AV lead for pacing and/or cardioversion/defibrillation comprising atrial and ventricular lead bodies combined together through an intermediate segment thereof. The proximal segment of the atrial lead branching from the intermediate segment is formed in accordance with the invention, and the permanently enclosed pull wire extends through the atrial lead body and may constitute an atrial lead conductor. The ventricular lead body accepts a removable stiffening stylet.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 7 is a perspective view of a second embodiment of the hand-held tool related with the proximal segment of the cardiac lead of FIGS. 1–3 to receive the proximal segment and stretch it;

FIG. 8 is an end view of the second embodiment of the hand-held tool of FIG. 7 receiving the lead body proximal segment;

FIG. 9 is an end view of a variation of the second embodiment of the hand-held tool of FIG. 7 receiving the lead body proximal segment;

DETAILED DESCRIPTION OF THE PREFERRED EMBODIMENTS

Figure 1:
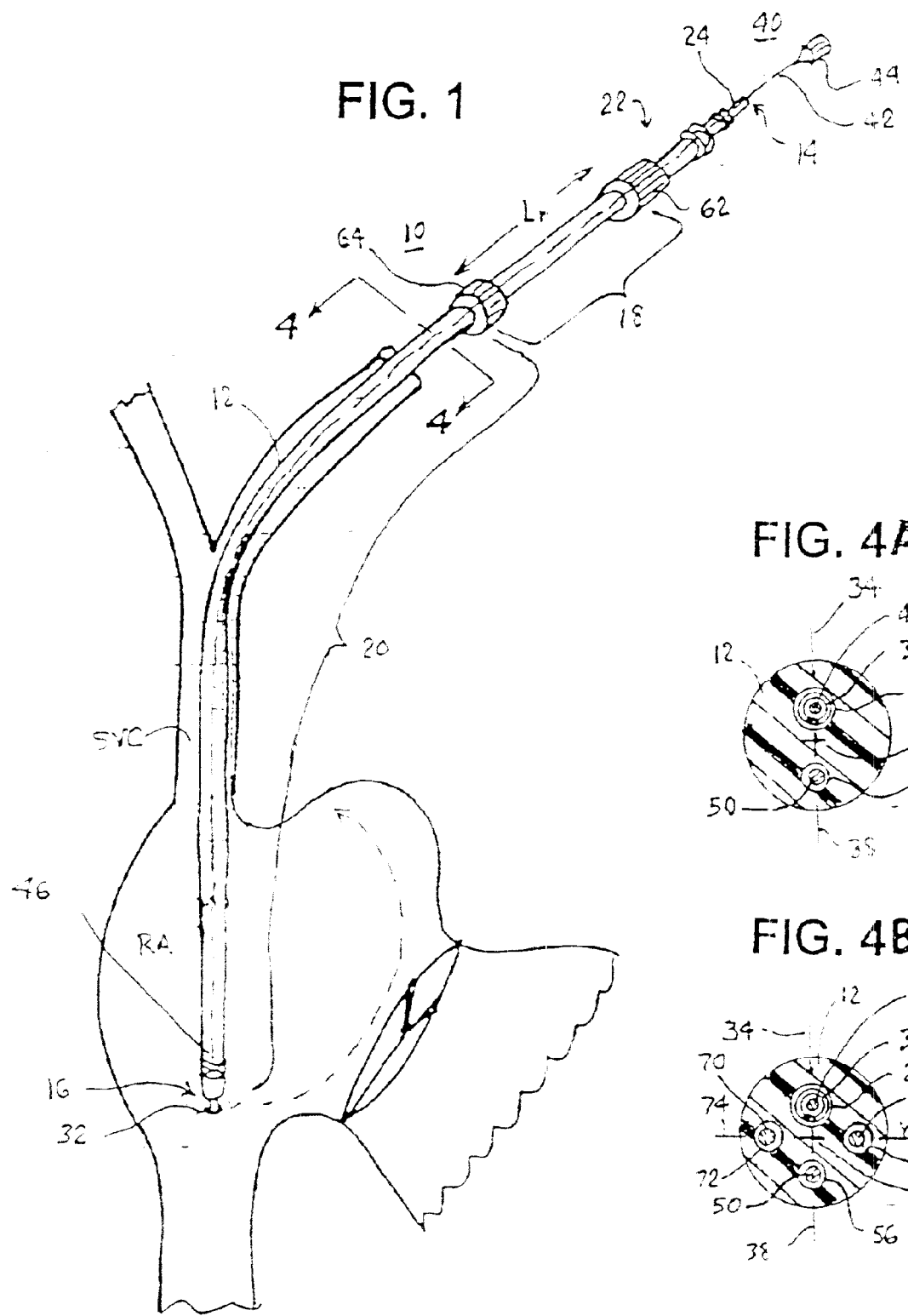
FIG. 1 is a simplified perspective view illustrating the introduction of a cardiac lead of the present invention into the right atrium employing a stiffening stylet.

In the following detailed description, references are made to illustrative embodiments for carrying out the invention. It is understood that other embodiments may be utilized without departing from the scope of the invention. The preferred embodiments of the invention are described in relation to endocardial cardiac leads, particularly endocardial pacing and/or cardioversion/defibrillation leads, but it will be understood that the present invention can be utilized in any elongated medical instruments of the types described or mentioned herein and equivalents that may presently exist or come into existence in the future.

Thus, FIGS. 1 through 4B illustrate an exemplary unipolar, bipolar or multi-polar pacing and/or cardioversion/defibrillation lead 10 in which the principles of the invention are illustrated employing a stiffening stylet 40 and a hand tool of the types described further below. Such endocardial pacing and cardioversion leads typically comprise a length of coiled wire conductor formed around an axial lumen and encased within a suitable insulating material, such as silicone rubber or polyurethane, that is substantially inert to body fluids and tissues. A hollow connector pin is attached coaxially to the lumen and electrically to the proximal end of the conductor. An electrically conductive electrode at the distal end of the conductor is adapted to be placed in contact with the endocardium or within the coronary sinus of the patient. When more than one length of separately-insulated coiled wire conductors is employed in modern pacing and cardioversion leads, each coiled wire conductor is wound coaxially around the centrally-disposed lumen which extends through the connector pin and the corresponding lengths of coiled wire conductors to the distal end of the lead body. The lumen receives the stiffening stylet of cylindrical wire for imparting stiffness and curvature to the distal portion of the lead body to facilitate its advancement through the venous system and to the desired internal site. Further details of the construction and utility of such endocardial pacing leads may be obtained from U.S. Pat. Nos. 4,506,680, 4,577,642, 4,606,118, and 4,711,281, for example.

In the present embodiment, the lead 10 comprises an elongated lead body 12 extending a predetermined length between lead body proximal end 14 and lead body distal end 16. The lead body 12 is divided along its length into a proximal segment 18 and a distal segment 20. A connector assembly 22 proximal to the proximal segment 20 comprises at least a connector pin 24, in unipolar embodiments, one ring-shaped connector element 26 in bipolar embodiments and one or more additional ring-shaped connector element in multi-polar embodiments.

Figure 4A:
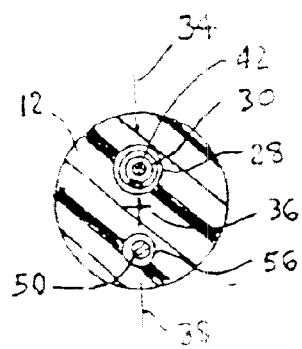
FIGS. 4A and 4B are cross-section views taken along lines 4—4 of FIGS. 1–3 illustrating the diametrically disposed radial offsets of the internal pull wire within the pull wire lumen from the lead body axis and the stylet and coiled wire conductor within the stylet lumen.
Figure 4B:
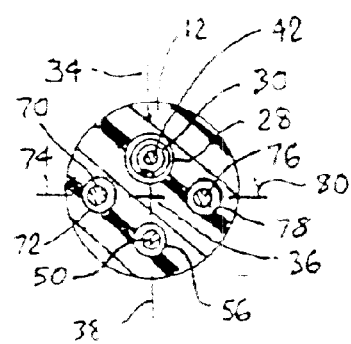

The elongated lead body 12 is formed of an insulative sheath of bio-compatible material as shown in FIGS. 4A and 4B that encloses a stylet lumen 28 that extends from a stylet lumen proximal end opening of the connector pin 24 to a stylet lumen distal end at the lead body distal end 16. A lead conductor 30 extends between the proximal connector pin 24 to a distal cardiac electrode 32. The lead conductor 30 is preferably formed of a loose wound coiled wire fitted within the stylet lumen 28.

The distal cardiac electrode 32 is simply shown schematically and can comprise a pace/sense electrode or a cardioversion/defibrillation electrode, and the type of electrode is immaterial to the present invention. In atrial and ventricular lead embodiments, passive or active fixation mechanisms of any of the know types for lodging in trabeculae or invading the myocardium can also be incorporated into the distal segment. Such fixation mechanisms are not employed typically in such cardiac leads introduced into the coronary sinus and great vein.

The stylet 40 comprises a stiff, straight, stylet wire 42 extending between a stylet handle 44 and a stylet wire distal end 46 that is adapted to be introduced through the stylet lumen 28, in this case within the coiled wire of conductor 30 to stiffen the lead body during introduction. In accordance with the present invention, the degree and length of curvature induced in the distal segment 20 depends upon the length of the stylet wire 42 advanced through a proximal portion of the distal segment while tension is applied to the proximal segment 18. The stylet lumen extending through the lead body 12 distal to the connector assembly 20 is preferably offset radially in radial direction 34 from the lead body axis 36.

The lead body 12 also encloses an elongated, inelastic, pull wire 50 extending through a pull wire lumen 56 that is off axis in a radial direction 38 from the medical instrument axis 36 and extends through the lead body proximal and distal segments 18 and 20. The pull wire 50 and the stiffening stylet wire 40 are displaced from one another by and 180° and radially displaced from the lead body axis 36. The pull wire 50 is attached at a proximal attachment point at or near the lead body proximal end 14, preferably within the connector assembly 22 and at a distal attachment point 54 at or near the instrument body distal end 16.

Figure 3:
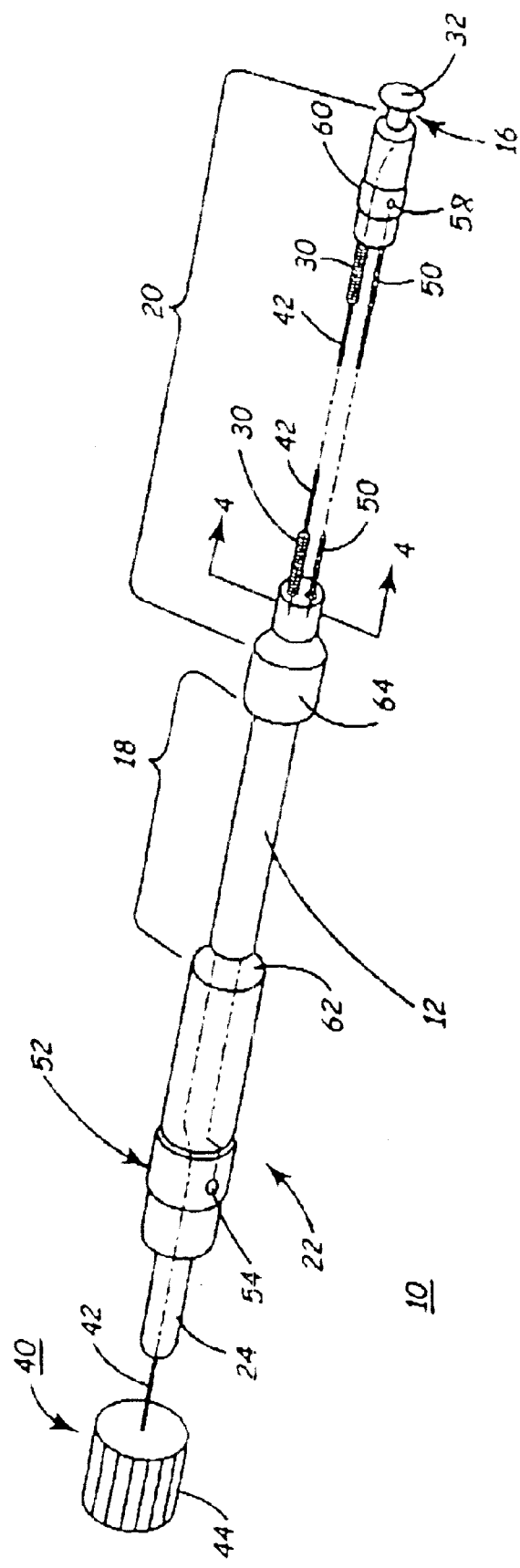
FIG. 3 is a simplified perspective view of a bipolar cardiac lead of the present invention.

In this bipolar or in multi-polar embodiments, the pull wire 50 can function as the lead conductor between a respective connector element and cardiac electrode. For example, FIG. 3 is a perspective simplified view of a bipolar cardiac lead 10 of the present invention illustrating the pull wire 50 electrically and mechanically attached at a proximal attachment point 54 with a ring-shaped connector element 52 and at a distal attachment point 58 to ring-shaped pace/sense electrode 60.

The present invention may be applied to multi-polar cardiac leads having additional proximal connector elements and distal electrodes that are electrically connected together by lead conductors encased within separate lumens of the lead body 12 or in separately insulated, multi-filar coiled wires interleaved in a common diameter coil winding with coiled wire conductor 30 in a manner well known in the art. Alternatively, FIG. 4B depicts separate coiled wire or straight conductors 70 and 76 extending through respective lumens 72 and 78 of the lead body 12 that are disposed radially in radial directions 74 and 80, respectively that are displaced orthogonally from radial directions 34 and 38. Therefore, the conductors 70 and 76 remain relatively un-tensioned when a bend in the radial direction 38 is imparted as described herein. It will be understood that the coiled wire conductor 30 can also be eliminated from the stylet lumen 28.

The stylet lumen 28 and the pull wire lumen 56 need only to be are offset in the radial directions 34 and 38, respectively, in the distal segment 20 or in a distal portion thereof that is intended to be bent in the radial direction 38 and can be otherwise disposed within the lead body 12 in other segments or portions thereof and in the connector element 22.

The lead body 12 is formed of an elastic material at least in the proximal segment 18 thereof that can be stretched or extended axially when tension is applied between proximal and distal ends of the proximal segment 18 so as to increase the length of the proximal segment 18 from the relaxed length depicted in FIG. 1. The applied tension is transferred to the inelastic pull wire 50 which counters the extension of the proximal segment by bending the instrument body distal segment 20 in the radial direction 38 away from the instrument body axis 36. The coil turns of the conductor 30 are loosely wound and are capable of stretching and compressing axially within the stylet lumen 28 as the distal segment 20 is bent when the proximal segment 18 is stretched and returns to its normal straight shape when tension is released from the proximal segment 18 and it resumes its relaxed length. The distal segment 20 may be slightly compressed, e.g., about 3% in length, when the proximal segment is stretched about 25%–30%.

The lead body 12 is therefore preferably formed of an elastic, bio-compatible material, e.g., medical grade silicone rubber capable of stretching axially by about 25%–30% in the proximal segment 18. Or the distal segment 20 can be formed of a relatively inelastic material, e.g., medical grade polyurethane that resists axial stretching or contraction, and the proximal segment 18 can formed of the more elastic silicone rubber that is capable of elastically stretching axially over the maximal length of the proximal segment 18 without any damage. The proximal and distal segments 18 and 20 can be adhered together at their abutting ends, and the junction can be reinforced by a thin sleeve adhered over the abutting ends in a manner well known in the art.

Preferably, the proximal segment 18 is bounded by enlarged proximal and distal rings or other structures 62 and 64 presenting shoulders that are adapted to be fitted into a hand-held tool of the types described below to thereby engage the proximal and distal ends of the proximal segment 18. Manipulation of the tool applies a selective amount of tension that stretches the proximal segment 18 from its relaxed length depicted in FIG. 1 to an elongated length depicted in FIG. 2 upon manual manipulation of the hand-held tool.

Figure 2:
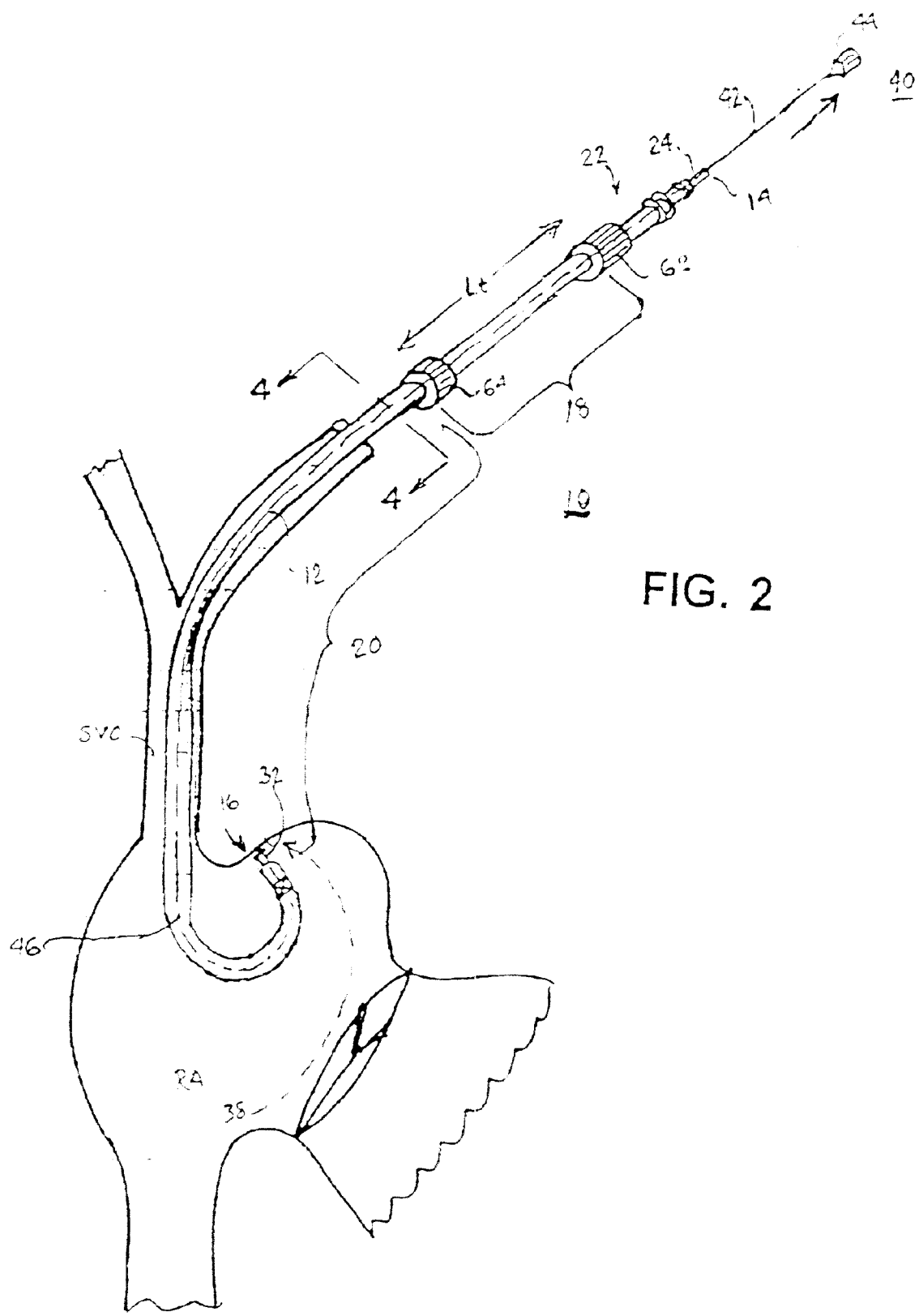
FIG. 2 is a simplified perspective view illustrating the formation of a J-shaped curve in the distal segment of the cardiac lead of FIG. 1 to direct the lead distal end electrode into the right atrial appendage by retracting the stiffening stylet and stretching a proximal segment of the lead body.

In this respect, FIG. 1 depicts the extension of the stylet wire distal end 46 to the stylet lumen distal end whereby the lead body 12 is relatively straight, depending upon any curvature of the stylet wire 42. The stylet wire 42 is adapted to be retracted proximally as tension is applied to the proximal segment to lengthen it from its relaxed length $L_T$ to a tensioned length $L_t$. FIG. 2 illustrates the effect of withdrawing the stylet wire 42 and applying tension between the proximal and distal ends of the proximal segment 18 and lengthening the segment length to the tensioned length $L_t$, whereby the curve or bend is imparted in the radial direction 38.

In this illustrated embodiment, the cardiac lead 10 is being implanted so that its distal electrode is lodged in the right atrial appendage. The stylet wire distal end 46 is advanced toward the lead body distal end 16 or retracted therefrom while tension is applied to stretch the lead body proximal segment 18 to the extent found useful to impart slight curves or deflect the distal tip during transvenous introduction to traverse bends in the venous pathway. In this way, the lead distal end is introduced through the SVC into the right atrium as depicted in FIG. 1. The J-shaped curvature of up to 220° in the radial direction 38 is then imparted as described above and depicted in FIG. 2. The stylet wire 42 is retracted in FIG. 2 to extend only through a proximal portion of the distal segment 20, and the bend is therefore constrained to form only in a distal portion of the distal segment 20. The distal electrode 32 is advanced into the trabeculae of the right atrial appendage whereby passive fixation tines engage with the trabeculae or an active fixation mechanism is engaged to attach to the myocardium or endocardial wall in any of the manners known in the art. The stylet 40 can be withdrawn and the tension applied to the proximal segment 18 can be released in any order. Similar procedures can be employed to locate the distal electrode 32 anywhere within the right heart chambers or into the coronary sinus.

It will be understood from the above that the present invention can be embodied in any of the above-referenced elongated medical instruments wherein the stylet lumen only receives the stylet and does not include an electrical conductor.

The proximal segment 18 is stretched preferably by use of a hand tool that receives the lead body 12, e.g., as within the proximal segment 18, so that the enlarged proximal and distal rings or other enlarged structures 62 and 64 present shoulders against outer surfaces of the tool that are spread apart by manipulation of a spanner extending between the outer surfaces. The hand tool can be manipulated using one hand to deflect the lead body distal end and to impart a curve in the distal portion of the lead body distal segment 20 after the stiffening stylet wire is retracted to only extend through the proximal portion of the lead body distal segment 20.

Figure 5:
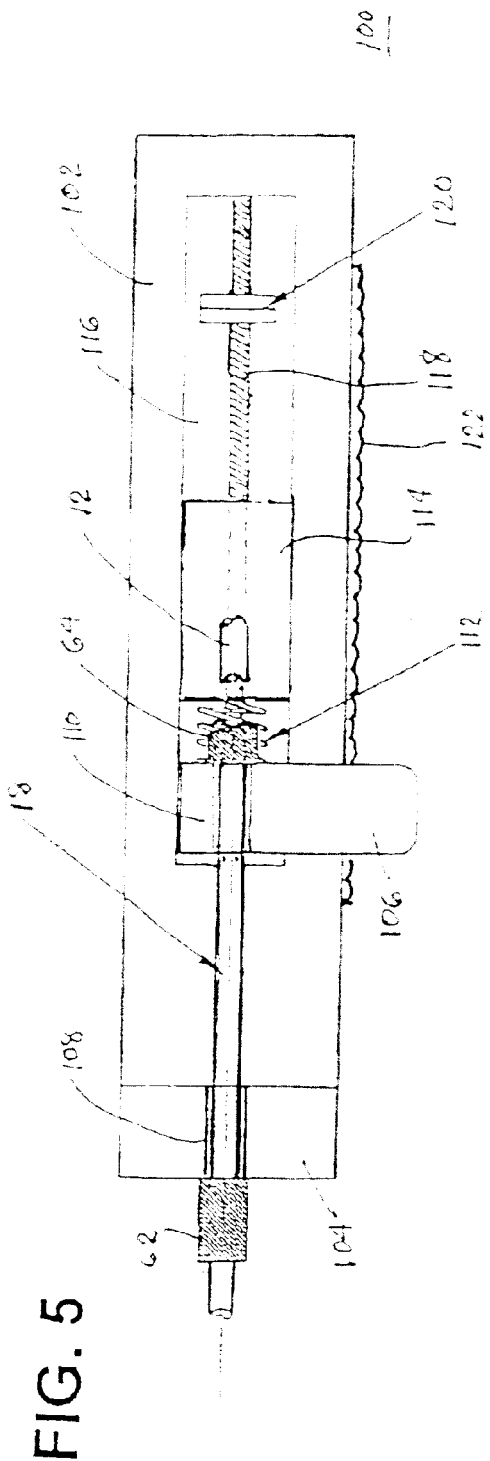
FIG. 5 is a top view of a first embodiment of a hand-held tool engaged with the proximal segment of the cardiac lead of FIGS. 1–3 to stretch the proximal segment and impart a curve in the distal segment as illustrated in FIG. 2.
Figure 6:
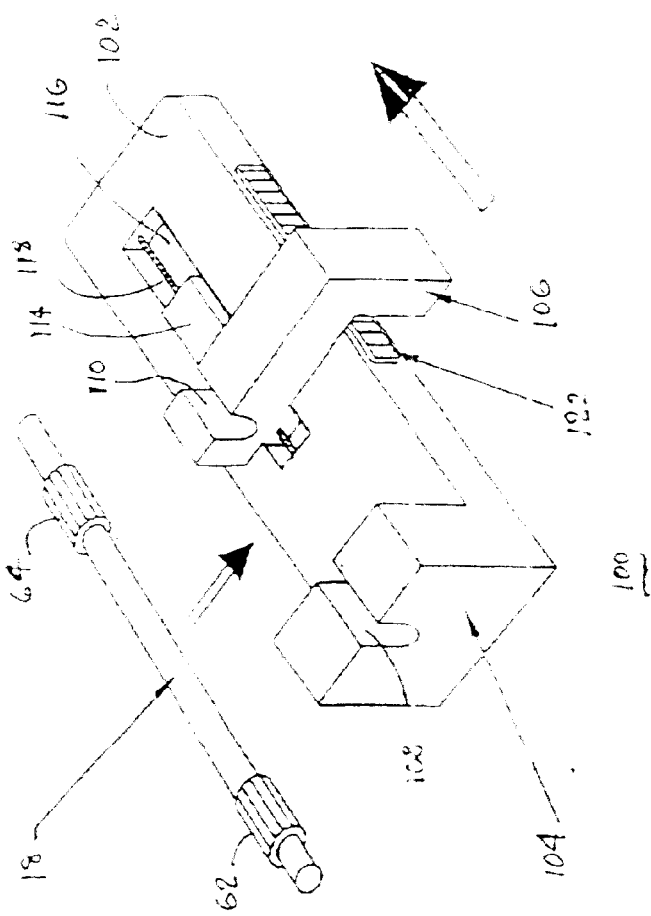
FIG. 6 is a perspective view of the first embodiment of the hand-held tool of FIG. 5 related with the proximal segment of the cardiac lead of FIGS. 1–3 to receive the proximal segment.

FIGS. 5 and 6 illustrate construction, use and function of a first embodiment hand-held tool 100 adapted to be engaged with the proximal segment 18 of the cardiac lead 10 to stretch the proximal segment 18 and impart a curve in the distal segment 20 as illustrated described above. Hand held tool 100 comprises a frame 102 that supports a fixed cradle 104 and a movable shuttle 106 restrained within and movable along elongated recess 116. The fixed cradle 104 and movable shuttle 106 have notches 108 and 110 that are sized to receive the lead body 12 within the proximal segment 18 so that the enlarged proximal and distal rings or other enlarged structures 62 and 64 present shoulders against outer surfaces of the cradle 104 and shuttle 106, respectively, for example. It will be understood that the orientation of the lead body 12 to the cradle 104 and shuttle 106 can be reversed.

The structure 64 is shown in part to expose a spring 112 that is attached between the shuttle 106 and a block 114 that is supported within an elongated recess 116 in frame 102 to move back and forth along a threaded rod 118. The threaded rod 119 extends the length of the elongated recess 116 and extends through a portion of the shuttle 106, the spring 112 and the block 114. A rotatable stop 120 is provided along the threaded rod 118 that can be adjusted to prevent further movement of block 114 and to limit the maximum tensioned length $L_t$. The spring 112 collapses when force is applied to shuttle 106 that would otherwise over-tension the pull wire 50. The force can be inadvertently applied if the physician happens to retract the entire lead 10 and tool 100 proximally particularly, if a deployed distal fixation mechanism is not first released.

A friction strip 122, e.g., a strip of rubber, interference fits and frictionally engages against an inner surface of the shuttle 106 so that the stretched length $L_t$ of the proximal segment 18 can be maintained when hand pressure is released from shuttle 106. The physician must overcome the frictional resistance of the friction strip 122 to move the shuttle 106 back to the starting position to release the tension applied to stretch the proximal segment 18.

The stop 120 and spring 112 are optionally included and FIG. 6 shows a variation wherein they are not included and block 114 is optionally combined with shuttle 106.

FIGS. 7 and 8 illustrate a further hand-held tool 130 that receives the proximal segment 18 of the cardiac lead 10 of FIGS. 1-3 and stretches it axially as the two spring bands 132 and 134 are manually squeezed together. The opposite ends of the spring bands 132 and 134 are attached to opposed sides of extension blocks 136 and 138, respectively, that move apart as spring bands 132 and 134 are manually squeezed together. The proximal segment 18 is inserted through slots 136 and 138, respectively, of retention blocks 132 and 134 so that the enlarged proximal and distal rings or other enlarged structures 62 and 64 present shoulders against outer surfaces of the extension blocks 136 and 138, respectively.

FIG. 9 illustrates a further hand-held tool 150 receiving the lead body proximal segment 18 wherein additional spring bands 144 and 146 are joined orthogonally to the retention blocks 132 and 134. Elongated slots, e.g. slot 148 are provided through spring band 146 to locate the enlarged proximal and distal rings or other enlarged structures 62 and 64 present shoulders against outer sides of the extension blocks 136 and 138, respectively.

In use, the spring bands 132 and 134 or 132, 134, 144 and 146 are manually squeezed or pressed together to push the extension blocks 12 and 134 apart and thereby stretch the proximal segment 18 as described above.

Figure 10:
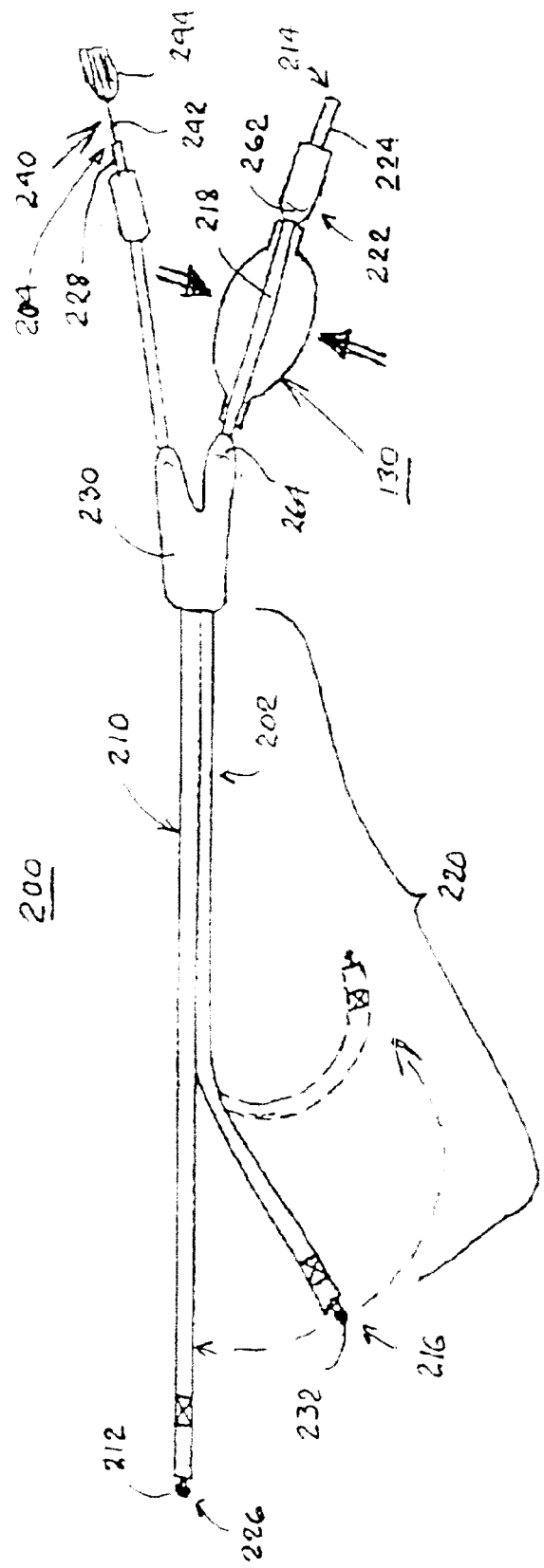
FIG. 10 is a side view of a single pass AV lead incorporating the invention.

FIG. 10 is a side view of a single pass AV lead 200 incorporating the invention for pacing and/or cardioversion/defibrillation comprising an atrial lead body 202 and a ventricular lead body 210 combined together through an intermediate segment thereof extending distally from Y-connector 230. The single pass AV lead 200 is advanced into the right atrium employing stylet 240 and with the atrial lead body distal segment 202 alongside the ventricular lead body 210. The atrial lead body distal segment 202 can be deflected or curved in the manner described above in the right atrium while the ventricular lead body distal end 226 is advanced into the right ventricle.

The ventricular lead body 210 extends between electrode 212 at ventricular lead body distal end 226 bearing one or more electrode 212 and fixation mechanism (not shown) to the connector pin 228 at the ventricular lead body proximal end 204. The ventricular lead body 210 can be formed employing any combination of pace/sense and/or cardioversion/defibrillation electrodes, distal fixation mechanisms, lead conductors, and proximal connector assembly configurations known in the art. The ventricular lead body has a lead body lumen that accepts stylet wire 242 of stylet 240 that can be manipulated using stylet handle 244 to advance the single pass AV lead 200 and to deploy an active fixation mechanism if provided at the ventricular lead body distal end 226 in a manner well known in the art.

The atrial lead body 202 extends between the atrial lead body distal end 216 bearing one or more electrode 232 and fixation mechanism (not shown) to the proximal connector assembly 222 and connector pin 224 at atrial lead body proximal end 214. The fixation mechanism can be either a passive fixation mechanism that self deploys, e.g., flexible pliant tines, or an active fixation mechanism that is deployed out of the atrial lead body distal end 216, e.g., a helical fixation mechanism. The helical fixation mechanism is typically deployed by rotation distally out of a protective sheath employing a stylet extended through a stylet lumen of the atrial lead body 202 after the atrial lead body distal end 216 is directed into the atrial appendage by forming a curve in atrial lead body distal segment 220 as shown in broken lines in FIG. 10. Therefore, the atrial lead body 202 may be formed with a stylet lumen for receiving a stylet that rotates a helical fixation mechanism or may not include a stylet lumen if a passive fixation mechanism or no fixation mechanism is provided at the atrial lead body distal end 216. If a stylet lumen is provided, a stylet may be employed in the atrial lead body lumen during introduction through the venous pathway into the right atrium and then withdrawn.

In this single pass AV lead embodiment, the atrial lead body proximal segment 218 branching from the intermediate segment a Y-connector 230 is formed in accordance with the invention. A permanently enclosed pull wire 50 extends through a pull wire lumen 56 as described above with respect to FIGS. 4A and 4B through the atrial lead body proximal and distal segments 218 and 220 and may operate as a lead conductor as described above in unipolar and multi-polar atrial lead embodiments.

The atrial lead body proximal segment 218 is bounded in this case by shoulder 262 of the connector assembly 222 and shoulder 264 of the Y-connector 230. The atrial lead body distal end 216 can be deflected and the atrial lead body distal segment 220 can be curved as shown in broken lines in FIG. 10 by employing a hand-held tool, e.g., tool 130 of FIG. 7, employed as described above. It would also be possible to manually grasp the atrial lead body connector assembly 222 and the Y-connector to pull them apart to stretch the atrial lead body proximal segment 218.

It will be understood that the principles of the above invention can be readily implemented into catheters and guide wires wherein the radially offset pull wire extending through a pull wire lumen can be fixed at proximal and distal ends of the catheter or guide wire, and a flexible proximal segment thereof can be stretched to cause a bend to be incurred in the distal segment. The bend can be controlled by use of a stiffening stylet inserted through another lumen radially opposed to the pull wire lumen. In many guide wires and catheters, the instrument body is mechanically reinforced to provide column strength and stiffness that provides "pushability" of the instrument body through a vascular pathway or other often tortuous pathway through the body. Often, a relatively short distal segment or the distal tip is relatively soft and/or flexible compared to one or more proximally disposed segments, and the most proximal segment is quite resistant to bending and axial stretching or compression. In such cases, the above-described embodiments of the stretchable proximal segments can be incorporated either in-line with the remainder of the instrument body or incorporated as a branch or a side-arm in a proximal portion thereof that remains outside the body in use to be manipulated as described above.

It will also be understood that the hand tools as described above may be modified to frictionally grip or engage the proximal and distal ends of the proximal segment rather than bear against an enlarged diameter of the instrument body, whereby the instrument body can be of constant diameter throughout its length or in the proximal portion thereof.

It will also be understood that while the hand-held tools described herein offer many conveniences, the present invention can be practiced employing mechanized instruments to engage the instrument body proximal segment and stretch it to deflect the instrument body distal end or impart a curve in the instrument body distal segment Such mechanized instruments can be operated at the operating site by medical personnel or remotely operated through in a robotic manner.

Conclusion

All patents and publications referenced herein are hereby incorporated by reference in their entireties.

It will be understood that certain of the above-described structures, functions and operations of the above described preferred embodiments are not necessary to practice the present invention and are included in the description simply for completeness of an exemplary embodiment or embodiments. It will also be understood that there may be other structures, functions and operations ancillary to the typical operation of elongated medical instruments that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. An elongated medical instrument to be advanced through the body comprising:

an instrument body extending between an instrument body proximal end and an instrument body distal end and having an instrument body proximal segment and an instrument body distal segment, the instrument body having an instrument body axis extending axially in the instrument body distal segment and further comprising an elongated pull wire lumen extending through the instrument body proximal segment and instrument body distal segment, the pull wire lumen extending in parallel with and radially offset in a first radial direction from the instrument body distal axis in the instrument body distal segment;

an inelastic pull wire extending through the pull wire lumen from a pull wire proximal attachment with the elongated medical instrument to a pull wire distal attachment with the instrument body distal segment;

the instrument body proximal segment is formed of an elastic material capable of being stretched axially under axially applied tension applied directly at the instrument body proximal segment, whereby the inelastic pull wire bends in the first radial direction and thereby imparts a curve to the instrument body in the instrument body distal segment; and proximal tension applying means coupled to the instrument body proximal segment at a proximal site of the instrument body proximal segment and distal tension applying means coupled to the instrument body proximal segment at a distal site of the instrument body proximal segment, the proximal and distal tension applying means separated apart by a relaxed length of the instrument body proximal segment, wherein tension is adapted to be applied axially between the proximal and distal tension applying means and transferred to the instrument body proximal segment to stretch it to a tensioned length of the instrument body proximal segment exceeding the relaxed length.

2. The elongated medical instrument of claim 1, wherein the instrument body further comprises means for restraining the length of the curve imparted in the instrument body distal segment.

3. The elongated medical instrument of claim 1, wherein the instrument body further comprises an elongated stylet lumen extending from a stylet lumen proximal end opening through the instrument body proximal segment and instrument body distal segment to a stylet distal end, the stylet lumen extending in parallel with and radially offset in a second radial direction from the instrument body distal axis in the instrument body distal segment, whereby a relatively straight stylet wire of a stylet can be inserted through the stylet lumen proximal end opening and advanced distally through a selected proximal portion of the instrument body distal segment to constrain the formation of the curve to the distal portion of the instrument body distal segment.

4. An elongated medical instrument to be advanced through the body comprising:
  an instrument body extending between an instrument body proximal end and an instrument body distal end and having an instrument body proximal segment and an instrument body distal segment, the instrument body having an instrument body axis extending axially in the instrument body distal segment and further comprising an elongated pull wire lumen extending through the instrument body proximal segment and instrument body distal segment, the pull wire lumen extending in parallel with and radially offset in a first radial direction from the instrument body distal axis in the instrument body distal segment;
  an inelastic pull wire extending through the pull wire lumen from a pull wire proximal attachment with the elongated medical instrument to a pull wire distal attachment with the instrument body distal segment, wherein the instrument body proximal segment is formed of an elastic material capable of being stretched axially under axially applied tension applied directly at the instrument body proximal segment, whereby the inelastic pull wire bonds in the first radial direction and thereby imparts a curve to the instrument body in the instrument body distal segment, wherein the instrument body further comprises an elongated stylet lumen extending from a stylet lumen proximal end opening through the instrument body proximal segment and instrument body distal segment to a stylet distal end, the stylet lumen extending in parallel with and radially offset in a second radial direction from the instrument body distal axis in the instrument body distal segment, whereby a relatively straight stylet wire of a stylet can be inserted through the stylet lumen proximal end opening and advanced distally through a selected proximal portion of the instrument body distal segment to constrain the formation of the curve to the distal portion of the instrument body distal segment, and wherein the instrument body in the instrument body proximal segment has an instrument body diameter and further comprising an enlarged diameter proximal tension applying ring coupled to the instrument body proximal segment at a proximal site of the instrument body proximal segment and an enlarged diameter distal tension applying ring coupled to the instrument body proximal segment at a distal site of the instrument body proximal segment, the proximal and distal tension applying rings separated apart by a relaxed length of the instrument body proximal segment, wherein tension is adapted to be applied axially between the proximal and distal tension applying rings and transferred to the instrument body proximal segment to stretch it to a tensioned length of the instrument body proximal segment exceeding the relaxed length.

5. An elongated medical instrument to be advanced through the body comprising:
  an instrument body extending between an instrument body proximal end and an instrument body distal end and having an instrument body proximal segment and an instrument body distal segment, the instrument body having an instrument body axis extending axially in the instrument body distal segment and further comprising an elongated pull wire lumen extending through the instrument body proximal segment and instrument body distal segment, the pull wire lumen extending in parallel with and radially offset in a first radial direction from the instrument body distal axis in the instrument body distal segment;
  an inelastic pull wire extending through the pull wire lumen from a pull wire proximal attachment with the elongated medical instrument to a pull wire distal attachment with the instrument body distal segment; and
  the instrument body proximal segment is formed of an elastic material capable of being stretched axially under axially applied tension applied directly at the instrument body proximal segment, whereby the inelastic pull wire bends in the first radial direction and thereby imparts a curve to the instrument body in the instrument body distal segment, wherein the instrument body in the instrument body proximal segment has an instrument body diameter and further comprising an enlarged diameter proximal tension applying ring coupled to the instrument body proximal segment at a proximal site of the instrument body proximal segment and an enlarged diameter distal tension applying ring coupled to the instrument body proximal segment at a distal site of the instrument body proximal segment, the proximal and distal tension applying rings separated apart by a relaxed length of the instrument body proximal segment, wherein tension is adapted to be applied axially between the proximal and distal tension applying rings and transferred to the instrument body proximal segment to stretch it to a tensioned length of the instrument body proximal segment exceeding the relaxed length.

6. The elongated medical instrument of claim 1, wherein the medical instrument comprises an electrical medical lead.

7. The elongated medical instrument of claim 1, wherein the medical instrument comprises a guide wire.

8. The elongated medical instrument of claim 1, wherein the medical instrument comprises a catheter.

9. An elongated electrical medical lead to be advanced through the body comprising:

a lead body extending between a lead body proximal end and a lead body distal end and having a lead body proximal segment and a lead body distal segment, the lead body having a lead body axis extending axially in the lead body distal segment and further comprising an elongated pull wire lumen extending through the lead body proximal segment and lead body distal segment, the pull wire lumen extending in parallel with and radially offset in a first radial direction from the lead body distal axis in the lead body distal segment;

a proximal connector element at the lead body proximal end;

an electrode at the lead body distal end;

an elongated electrical conductor extending between the proximal connector element and the electrode through and enclosed within the lead body;

an inelastic pull wire extending through the pull wire lumen from a pull wire proximal attachment with the elongated medical lead to a pull wire distal attachment with the lead body distal segment;

the lead body proximal segment is formed of an elastic material capable of being stretched axially under axially applied tension applied directly at the instrument body proximal segment, whereby the inelastic pull wire bends in the first radial direction and thereby imparts a curve to the lead body in the lead body distal segment to orient the electrode at a desired site in the body; and proximal tension applying means coupled to the lead body proximal segment at a proximal site of the lead body proximal segment and distal tension applying means coupled to the lead body proximal segment at a distal site of the lead body proximal segment, the proximal and distal tension applying means separated apart by a relaxed length of the lead body proximal segment, wherein tension is adapted to be applied axially between the proximal and distal tension applying means and transferred to the lead body proximal segment to stretch it to a tensioned length of the lead body proximal segment exceeding the relaxed length.

10. The elongated medical lead of claim 9, wherein the lead body further comprises means for restraining the length of the curve imparted in the lead body distal segment.

11. The elongated medical lead of claim 9, wherein the lead body further comprises an elongated stylet lumen extending from a stylet lumen proximal end opening through the lead body proximal segment and lead body distal segment to a stylet distal end, the stylet lumen extending in parallel with and radially offset in a second radial direction from the lead body distal axis in the lead body distal segment, whereby a relatively straight stylet wire of a stylet can be inserted through the stylet lumen proximal end opening and advanced distally through a selected proximal portion of the lead body distal segment to constrain the formation of the curve to the distal portion of the lead body distal segment.

12. An elongated electrical medical lead to be advanced through the body comprising:

a lead body extending between a lead body proximal end and a lead body distal end and having a lead body proximal segment and a lead body distal segment, the lead body having a lead body axis extending axially in the lead body distal segment and further comprising an elongated pull wire lumen extending through the lead body proximal segment and lead body distal segment, the pull wire lumen extending in parallel with and radially offset in a first radial direction from the lead body distal axis in the lead body distal segment;

a proximal connector element at the lead body proximal end;

an electrode at the lead body distal end;

an elongated electrical conductor extending between the proximal connector element and the electrode through and enclosed within the lead body;

an inelastic pull wire extending through the pull wire lumen from a pull wire proximal attachment with the elongated medical lead to a pull wire distal attachment with the lead body distal segment; and the lead body proximal segment is formed of an elastic material capable of being stretched axially under axially applied tension applied directly at the instrument body proximal segment, whereby the inelastic pull wire bends in the first radial direction and thereby imparts a curve to the lead body in the lead body distal segment to orient the electrode at a desired site in the body, wherein the lead body further comprises an elongated stylet lumen extending from a stylet lumen proximal end opening through the lead body proximal segment and lead body distal segment to a stylet distal end, the stylet lumen extending in parallel with and radially offset in a second radial direction from the lead body distal axis in the lead body distal segment, whereby a relatively straight stylet wire of stylet can be inserted through the stylet lumen proximal end opening and advanced distally through a selected proximal portion of the lead body distal segment to constrain the formation of the curve to the distal portion of the lead body distal segment, wherein the lead body in the lead body proximal segment has a lead body diameter and further comprising an enlarged diameter proximal tension applying ring coupled to the lead body proximal segment at a proximal site of the lead body proximal segment and an enlarged diameter distal tension applying ring coupled to the lead body proximal segment at a distal site of the lead body proximal segment, the proximal and distal tension applying rings separated apart by a relaxed length of the lead body proximal segment, wherein tension is adapted to be applied axially between the proximal and distal tension applying rings and transferred to the lead body proximal segment to stretch it to a tensioned length of the lead body proximal segment exceeding the relaxed length.

13. The elongated medical lead of claim 11, wherein the elongated electrical conductor extends through the stylet wire lumen.

14. The elongated medical lead of claim 13, further comprising:

a further proximal connector element at the lead body proximal end;

a further electrode at the lead body distal end; and wherein the pull wire is formed of a conductive material and is attached to the further proximal connector element and the further electrode and functions as a lead conductor.

15. The elongated medical lead of claim 9, further comprising:

a further proximal connector element at the lead body proximal end;

a further electrode at the lead body distal end; and wherein the pull wire is formed of a conductive material and is attached to the further proximal connector element and the further electrode and functions as a lead conductor.

16. An elongated electrical medical lead to be advanced through the body comprising:

a lead body extending between a lead body proximal end and a lead body distal end and having a lead body proximal segment and a lead body distal segment, the lead body having a lead body axis extending axially in the lead body distal segment and further comprising an elongated pull wire lumen extending through the lead body proximal segment and lead body distal segment, the pull wire lumen extending in parallel with and radially offset in a first radial direction from the lead body distal axis in the lead body distal segment;

a proximal connector element at the lead body proximal end;

an electrode at the lead body distal end;

an elongated electrical conductor extending between the proximal connector element and the electrode through and enclosed within the lead body;

an inelastic pull wire extending through the pull wire lumen from a pull wire proximal attachment with the elongated medical lead to a pull wire distal attachment with the lead body distal segment; and the lead body proximal segment is formed of an elastic material capable of being stretched axially under axially applied tension applied directly at the instrument body proximal segment, whereby the inelastic pull wire bends in the first radial direction and thereby imparts a curve to the lead body in the lead body distal segment to orient the electrode at a desired site in the body, wherein the lead body in the lead body proximal segment has a lead body diameter and further comprising an enlarged diameter proximal tension applying ring coupled to the lead body proximal segment at a proximal site of the lead body proximal segment and an enlarged diameter distal tension applying ring coupled to the lead body proximal segment at a distal site of the lead body proximal segment, the proximal and distal tension applying rings separated apart by the relaxed length of the lead body proximal segment, wherein tension is adapted to be applied axially between the proximal and distal tension applying rings and transferred to the lead body proximal segment to stretch it to the tensioned length of the lead body proximal segment exceeding the relaxed length.

17. A system for advancing an elongated medical instrument through the body comprising:

an elongated medical instrument comprising:

an instrument body extending between an instrument body proximal end and an instrument body distal end and having an instrument body proximal segment and an instrument body distal segment, the instrument body having an instrument body axis extending axially in the instrument body distal segment and further comprising an elongated pull wire lumen extending through the instrument body proximal segment and instrument body distal segment, the pull wire lumen extending in parallel with and radially offset in a first radial direction from the instrument body distal axis in the instrument body distal segment; and an inelastic pull wire extending through the pull wire lumen from a pull wire proximal attachment with the elongated medical instrument to a pull wire distal attachment with the instrument body distal segment;

the instrument body proximal segment is formed of an elastic material capable of being stretched axially under axially applied tension, whereby the inelastic pull wire bends in the first radial direction and thereby imparts a curve to the instrument body in the instrument body distal segment; and proximal tension applying means coupled to the instrument body proximal segment at a proximal site of the instrument body proximal segment and distal tension applying means coupled to the instrument body proximal segment at a distal site of the instrument body proximal segment, the proximal and distal tension applying means separated apart by a relaxed length of the instrument body proximal segment, tool means for engaging and applying tension axially between the proximal and distal tension applying means to stretch the instrument body proximal section to a tensioned length exceeding the relaxed length.

18. The system of claim 17, wherein the tool means further comprises means for restraining the tensioned length of the instrument body proximal segment.

19. The system of claim 17, wherein the instrument body further comprises an elongated stylet lumen extending from a stylet lumen proximal end opening through the instrument body proximal segment and instrument body distal segment to a stylet distal end, the stylet lumen extending in parallel with and radially offset in a second radial direction from the instrument body distal axis in the instrument body distal segment, whereby a relatively straight stylet wire of a stylet can be inserted through the stylet lumen proximal end opening and advanced distally through a selected proximal portion of the instrument body distal segment to constrain the formation of the curve to the distal portion of the instrument body distal segment.

20. The system of claim 17, wherein:

the instrument body in the instrument body proximal segment has an instrument body diameter;

the proximal tension applying means further comprises an enlarged diameter proximal tension applying ring coupled to the instrument body proximal segment at a proximal site of the instrument body proximal segment;

the distal tension applying means further comprises an enlarged diameter distal tension applying ring coupled to the instrument body proximal segment at a distal site of the instrument body proximal segment; and the tool means is adapted to engage and increase the separation between the proximal and distal tension applying rings to stretch the instrument body proximal segment to the tensioned length.

21. The system of claim 17, wherein the medical instrument comprises an electrical medical lead.

22. The system of claim 17, wherein the medical instrument comprises a guide wire.

23. The system of claim 17, wherein the medical instrument comprises a catheter.

24. A system for advancing an elongated medical instrument through the body comprising:

an elongated medical instrument comprising:

an instrument body extending between an instrument body proximal end and an instrument body distal end and having an instrument body proximal segment and an instrument body distal segment, the instrument body having an instrument body axis extending axially in the instrument body distal segment and further comprising an elongated pull wire lumen extending through the instrument body proximal segment and instrument body distal segment, the pull wire lumen extending in parallel with and radially offset in a first radial direction from the instrument body distal axis in the instrument body distal segment; and an inelastic pull wire extending through the pull wire lumen from a pull wire proximal attachment with the elongated medical instrument to a pull wire distal attachment with the instrument body distal segment;

the instrument body proximal segment is tubular having a predetermined segment diameter and is formed of an elastic material capable of being stretched axially under axially applied tension, whereby the inelastic pull wire bends in the first radial direction and thereby imparts a curve to the instrument body in the instrument body distal segment;

an enlarged diameter proximal tension applying ring coupled to the instrument body proximal segment at a proximal site of the instrument body proximal segment; and an enlarged diameter distal tension applying ring coupled to the instrument body proximal segment at a distal site of the instrument body proximal segment and separated from the proximal tension applying ring by a relaxed length of the instrument body proximal segment; and a hand-held tool having a first surface that engages the proximal tension applying ring and a second surface spaced from the first surface that engages the distal tension applying ring and a spanner extending between the first and second surfaces that can be manually adjusted to increase the spacing between the first and second surfaces to axially apply tension to and increase the length of the instrument body proximal segment.

25. The system of claim 24, wherein the hand-held tool further comprises a frame that supports a fixed cradle having a notch sized to receive the diameter of the instrument body proximal segment between the proximal and distal tension applying rings and supports a shuttle movable along the frame with respect to the fixed cradle, the shuttle having a notch sized to receive the diameter of the instrument body proximal segment between the proximal and distal tension applying rings, whereby one of the fixed cradle and the shuttle present the first surface to the proximal tension applying ring and the other of the fixed cradle and the shuttle presents the second surface to the distal tension applying ring, the frame supporting the cradle and shuttle functions as the spanner between the first and second surfaces, and the shuttle is manually movable along the frame to increase the spacing between the first and second surfaces to axially apply tension to and increase the length of the instrument body proximal segment.

26. The system of claim 25, wherein the hand-held tool further comprises a movable stop supported by the frame in the path of movement of the movable shutter that is adjustable to limit the maximum spacing that can be made between the first and second surfaces.

27. The system of claim 25, wherein the hand-held tool further comprises a spring load that limits the maximum tension that can be applied made between the proximal and distal rings.

28. The system of claim 24, wherein the spanner of the hand-held tool further comprises first and second elongated spring bands that extend between opposed first and second sides of first and second extension blocks, the first and second extension blocks present the first and second surfaces respectively parallel to one another, the first and second extension blocks having first and second slots, respectively, extending laterally across the first and second extension blocks intersecting the first and second surfaces and sized to receive the diameter of the instrument body proximal segment between the proximal and distal tension applying rings and to present the first surface to the proximal tension applying ring and the second surface to the distal tension applying ring, whereby the first and second surfaces are spread apart as the elongated spring bands are pressed toward one another to axially apply tension to and increase the length of the instrument body proximal segment.

29. The system of claim 28, wherein the spanner further comprises third and fourth spring bands extending between opposed third and fourth sides of the first and second extension blocks, whereby the first and second surfaces are spread apart as the first and second elongated spring bands are pressed toward one another and the third and fourth spring bands are pressed toward one another to axially apply tension to and increase the length of the instrument body proximal segment.

30. A system for advancing an elongated medical instrument through the body comprising:

an the elongated medical instrument adapted to be inserted into a pathway of the body, the elongated medical instrument comprising:

an instrument body extending between an instrument body proximal end and an instrument body distal end and having an instrument body proximal segment and an instrument body distal segment, the instrument body having an instrument body axis extending axially in the instrument body distal segment and further comprising an elongated pull wire lumen extending through the instrument body proximal segment and instrument body distal segment, the pull wire lumen extending in parallel with and radially offset in a first radial direction from the instrument body distal axis in the instrument body distal segment;

an inelastic pull wire extending through the pull wire lumen from a pull wire proximal attachment with the elongated medical instrument to a pull wire distal attachment with the instrument body distal segment; and the instrument body proximal segment is formed of an elastic material capable of being stretched axially under axially applied tension; and tension applying means operable as the distal end is advanced, for selectively applying axial tension directly at the instrument body proximal section to stretch the instrument body proximal segment whereby the inelastic pull wire bends in the first radial direction and thereby imparts a curve to the instrument body in the instrument body distal segment so as to deflect the distal end to the extent found expedient to advance the distal tip and to position the distal end at a remote site in the body.

31. The system of claim 30, further comprising:

means for selectively restraining the length of the curve imparted in the instrument body distal segment to effect the advancement and positioning of the distal end.

32. The system of claim 30, wherein the instrument body further comprises an elongated stylet lumen extending from a stylet lumen proximal end opening through the instrument body proximal segment and instrument body distal segment to a stylet distal end, the stylet lumen extending in parallel with and radially offset in a second radial direction from the instrument body distal axis in the instrument body distal segment, and further comprising:

a stylet having a relatively straight stylet wire adapted to be inserted through the stylet lumen proximal end opening and distally through a selected proximal portion of the instrument body distal segment to constrain the formation of the curve to the distal portion of the instrument body distal segment.

33. The system of claim 32, wherein the tension applying means further comprises a hand-held tool adapted to engage the proximal and distal ends of the proximal segment in its relaxed length and having means responsive to manual manipulation to apply a selective amount of tension that stretches the proximal segment from its relaxed length to a selected tensioned length that forms a curve of desired radius at least a distal portion of the distal segment.

34. The system of claim 30, wherein the tension applying means further comprises a hand-held tool adapted to engage the proximal and distal ends of the proximal segment in its relaxed length and having means responsive to manual manipulation to apply a selective amount of tension that stretches the proximal segment from its relaxed length to a selected tensioned length that forms a curve of desired radius at least a distal portion of the distal segment.

35. The system of claim 34, wherein the hand-held tool further comprises a frame that supports a fixed cradle adapted to engage one of the first and second ends of the instrument body proximal segment and supports a shuttle movable along the frame with respect to the fixed cradle, the shuttle adapted to engage the other of the first and second ends of the instrument body proximal segment, whereby the shuttle is manually movable along the frame to axially apply tension to and increase the length of the instrument body proximal segment.

36. The system of claim 35, wherein the hand-held tool further comprises a movable stop supported by the frame in the path of movement of the movable shutter that is adjustable to limit the maximum spacing that can be made between the first and second surfaces.

37. The system of claim 35, wherein the hand-held tool further comprises a spring load that limits the maximum tension that can be applied made between the proximal and distal rings.

38. The system of claim 34, wherein the hand-held tool further comprises first and second elongated spring bands that extend between opposed first and second sides of first and second extension blocks, the first extension block engaging one of the first and second ends of the instrument body proximal segment and the second extension block engaging the other of the first and second ends of the instrument body proximal segment, whereby the first and second extension blocks are spread apart as the elongated spring bands are pressed toward one another to axially apply tension to and increase the length of the instrument body proximal segment.

39. The system of claim 38, wherein the hand-held tool further comprises third and fourth spring bands extending between opposed third and fourth sides of the first and second extension blocks, whereby the first and second extension blocks are spread apart as the first and second elongated spring bands are pressed toward one another and the third and fourth spring bands are pressed toward one another to axially apply tension to and increase the length of the instrument body proximal segment.

40. The system of claim 30, wherein the medical instrument comprises an electrical medical lead.

41. The system of claim 30, wherein the medical instrument comprises a guide wire.

42. The system of claim 30, wherein the medical instrument comprises a catheter.

43. An elongated medical instrument, comprising:

an instrument body having a proximal segment and a distal segment, the proximal segment having a first length extending distally from a proximal end to a distal end and the distal segment extending distally from the distal end of the proximal segment, and the instrument body forming a first lumen extending through the proximal segment and the distal segment;

an elongated member extending through the first lumen of the instrument body;

a first member positioned at the proximal end of the proximal segment; and a second member positioned at the distal end of the proximal segment and spaced a first length from the first curve imparting member, wherein the proximal segment is advanced from the first length to a second length greater than the first length in response to axial tension being applied to at least one of the first member and the second member, and wherein a selective curvature is applied along the distal segment via the elongated member in response to the proximal segment being advanced to the second length.

44. The elongated medical instrument of claim 43, wherein the instrument body forms a second lumen extending through the proximal segment and the distal segment for positioning an insertable elongated member capable of being inserted within and advanced to a distal end of the distal segment through the second lumen, wherein the insertable elongated member is retracted from the distal end of the distal segment to extend through a portion of the distal segment so that the curvature is applied to a selected length of the distal segment.

45. The elongated medical instrument of claim 44, wherein the selected length extends from a distal end of the insertable elongated member to the distal end of the distal segment.

* * * * *